United States Patent [19]

Seiler et al.

[11] Patent Number: 4,571,427

[45] Date of Patent: Feb. 18, 1986

[54] METHOD OF PREPARING 2-CHLOROETHYLDICHLOROSILANES

[75] Inventors: Claus-Dietrich Seiler, Rheinfelden; Hans-Joachim Vahlensieck, Wehr, both of Fed. Rep. of Germany

[73] Assignee: Dynamit Nobel AG, Troisdorf Köln, Fed. Rep. of Germany

[21] Appl. No.: 644,770

[22] Filed: Aug. 27, 1984

[30] Foreign Application Priority Data

Aug. 31, 1983 [DE] Fed. Rep. of Germany ....... 3331372

[51] Int. Cl.$^4$ ............................ C07F 7/08; C07F 7/12; C07F 7/16
[52] U.S. Cl. ...................................................... 556/476
[58] Field of Search .......................................... 556/476

[56] References Cited

U.S. PATENT DOCUMENTS 3,801,614  4/1974  Lohmann et al. .................... 556/476
4,049,690  9/1977  Seiler et al. .......................... 556/476
4,405,804  9/1983  John et al. ............................ 556/476

Primary Examiner—Paul F. Shaver
Attorney, Agent, or Firm—Felfe & Lynch

[57] ABSTRACT

A method for the preparation of 2-chloroethyldichlorosilanes by the reaction of vinyldichlorosilanes with hydrogen chloride in the presence of ferric chloride or tantalum chloride is disclosed. In the presence of these anhydrous metal chlorides, this reaction can be performed in the temperature range between 30° and 90° C., without the formation to any appreciable extent of methyl or ethyl trichlorosilane or other cleavage products. The end products obtained can also be easily separated from the byproducts by vacuum distillation without the need to resort to additional measures. The vacuum distillation can also be performed in the presence of the metal chlorides.

8 Claims, No Drawings

METHOD OF PREPARING 2-CHLOROETHYLDICHLOROSILANES

BACKGROUND OF THE INVENTION

The subject matter of the present invention is a method for the preparation of 2-chloroethyldichlorosilanes by the reaction of vinyldichlorosilanes with hydrogen chloride in the presence of anhydrous metal chlorides.

German Auslegeschrift No. 22 39 412 discloses a method for reacting vinylmethyldichlorosilane with hydrogen chloride in the presence of anhydrous aluminum chloride to form 2-chloroethylmethyldichlorosilane. The reaction temperature, however, must be below 0° C., and the separation of the desired chloroethylmethyldichlorosilane by distillation from the byproducts and the aluminum chloride can be performed only with intense cooling of the produce receivers, because otherwise, at temperatures from 10° to 20° C., the chloroethyldichlorosilane degrades again with the formation of the starting products or of methyltrichlorosilane and ethylene.

To remedy these disadvantages, a method is described in German Offenlegungsschrift DE-OS No. 24 58 962 according to which the distillation is performed in the presence of alkali chlorides. If these measures are taken, the distillation can be performed up to bottom temperatures of 90° C. at pressures between 15 and 30 mbar; nevertheless, yields of a maximum of 71% are obtained, which thus are inadequate for technical purposes.

Furthermore, a method is known from German Offlegungsschrift DE-OS No. 31 44 020 for performing the reaction of the vinyldichlorosilane with hydrogen chloride in the presence of alkyl aluminum compounds, and performing the subsequent distillation in the presence of siloxanes. A disadvantage of this process is the circumstance that the hydrogen chloride addition must be performed at temperatures below 0° C. in order to limit the formation of methyl trichlorosilane and ethylene. In spite of the addition of siloxane, yields of only around 85% are obtained in the final distillation.

The problem therefore existed of conducting the reaction of vinyldichlorosilanes with hydrogen chloride to form chloroethyldichlorosilanes such that it will be possible to operate at room temperature of slightly elevated temperatures, that, in the reaction and subsequent distillation, the formation of byproducts such as methyl- or ethyltrichlorosilane or the re-formation of vinyldichlorosilanes will be largely prevented, and yields of more than 90% will be obtained.

THE INVENTION

As the solution to this problem, a method has now been found for the preparation of 2-chloroethyldichlorosilanes by the reaction of vinyldichlorosilanes with hydrogen chloride in the presence of anhydrous metal chlorides, which is characterized by using as metal chlorides ferric chloride or tantalum chloride, performing the reaction in the temperature range between 30° and 60° C. when ferric chloride is used, and in the range between 40° and 90° when tantalum chloride is used.

If this procedure is used, the formation of byproducts or degradation products is largely suppressed and the reaction to the desired 2-chloroethylsilanes is virtually quantitative. This is all the more surprising in that, when aluminum chloride is used as catalyst, in accordance with German Auslegeschrift No. 22 39 417, operating in the claimed temperature range, the formation of degradation products during the synthesis reaches amounts between 10 and 50% with respect to the input vinylmethyldichlorosilane.

The ferric chloride can be used in amounts between 1 and 15 wt. %., while amounts under 1 wt. % result in a reduced transformation to vinyldichlorosilanes. The preferred range of quantities of the ferric chloride is between 1 and 10% of the weight of the input vinyldichlorosilane. With these amounts the preferred temperature range is between 40° and 50° C.

Also, when tantalum chloride is used, the use of larger amounts leads to an increasing formation of degradation products. The amounts of tantalum chloride is therefore not to exceed 10%, if possible, of the weight of the input vinyldichlorosilane. The preferred range of amounts is between 1 and 5 percent of the weight of input vinyldichlorosilane. In this range, the reaction is performed preferably at temperatures between 65° and 80° C.

In the case of both metal chlorides, the formation of degradation products increases slightly at higher temperatures in conjunction with the use of larger amounts of metal chlorides. On the other hand, at lower temperatures the formation of degradation products is slightly reduced at the expense of a less complete transformation of the input product.

The reaction of the vinyldichlorosilanes with hydrogen chloride takes place at standard pressure. The use of slight excess pressure or vacuum is basically possible, but has no great influence on the reaction event.

The process of the invention can be performed either by the batch method or continuously. Its practical execution can be based on known methods. The metal chloride does not have to be used in solution or on a support, but can be in the form of a suspension in the reaction medium. Provision must of course be made for good, uniform distribution within the reaction medium.

The vinyldichlorosilanes that can be used as starting products have either a methyl or ethyl group or a vinyl group additionally on the silicon atom. Then either 2-chloroethylmethyl or 2-chloroethylethyl dichlorosilanes, or bis-(2-chloroethyl)-dichlorosilane, form as end products.

The separation of the desired end products from the reaction mixture can be performed by distillation without the use of additional measures. Preferably it is performed in vacuo at bottom temperatures of as much as about 80° C. The metal choride, however, does not need to be separated. Surprisingly, throughout the entire distillation, despite the unavoidable constant increase of the metal chloride content in the bottom of the still, no deterioration of the reaction product occurs. If the distillation of the desired chloroethyldichlorosilane is not performed until the bottom product is dry, the metal chloride remaining in the bottom can be used directly in a fresh batch without purifying operations.

The 2-chloroethyldichlorosilanes obtained by the claimed process, especially 2-chloroethylmethyldichlorosilane, are technically important intermediates for the preparation of compounds which are used in the agricultural field as adhesion mediators or for the modification of silicones. (U.S. Pat. No. 3,998,257)

EXAMPLES

EXAMPLE 1 For Purposes of Comparison

A cylindrical jacketed vessel made of glass (diam. 10 cm) with a 3-liter capacity, equipped with a stirrer, a gas introduction tube with frit, a thermometer and a reflux condenser, is charged with 2115 g (15) mol of vinylmethyldichlorosilane and 21 g of anhydrous ferric chloride. By means of a thermostat, a temperature of 20° C. is established in the interior of the reaction vessel, and then the introduction of the hydrogen chloride is begun through the frit placed at the bottom of the cylindrical vessel. Over a period of 6 hours a total of 584 g (16 mol) of hydrogen chloride is introduced. After this period the reaction is interrupted and a sample of the reaction liquid is tested by gas chromatography. Only 16% of the input vinylmethyldichlorosilane had reacted to form 2-chloroethylmethyldichlorosilane.

EXAMPLE 2 For Purposes of Comparison

In the apparatus of Example 1, the same amounts of vinylmethyldichlorosilane and hydrogen chloride are reacted at the same temperature and within the same time as in Example 1, but in the presence of 317 g of anhydrous ferric chloride. About 50% of the input vinylmethyldichlorosilane was converted to 2-chloroethylmethyldichlorosilane.

EXAMPLE 3 For Purposes of Comparison

In the apparatus of Example 1 the same amounts of vinylmethyldichlorosilane and hydrogen chloride are brought to reaction in the presence of the same amounts of ferric chloride and within the same time as in Example 1, but at temperatures of 70° C. About 65% of the input vinylmethyldichlorosilane was reacted to 2-chloroethylmethyldichlorosilane.

EXAMPLE 4 For Purposes of Comparison

In the apparatus of Example 1, the same amounts of vinylmethyldichlorosilane and hydrogen chloride and within the same time as in Example 1 were reacted, but in the presence of 317 g of anhydrous ferric chloride and at temperatures of 70° C. About 55% of the input vinylmethyldichlorosilane was transformed to 2-chloroethylmethyldichlorosilane.

EXAMPLES 5 to 12 (According to the Invention)

As in Example 1, the amounts of vinylmethyldichlorilane given therein are reacted with hydrogen chloride. The reaction temperatures and the catalyst concentrations are varied. The results are listed in Table 1.

Under the heading, "End Product Analysis," the percentages of the gas chromatogram areas of the components of the reaction solution are listed before and after separation of the catalyst. The separation of the catalyst was performed by distillation of the raw product.

Under the heading, "Yield," are listed the corresponding results of the fractional distillation of the raw synthesis products. The yield is given in percentages by weight of the input vinylmethyldichlorosilane.

EXAMPLE 13

2115 g of vinylmethyldichlorosilane and 105 g of ferric chloride are put into the apparatus of Example 1. At a reaction solution temperature of about 50° C., 584 g of hydrogen chloride is introduced over a period of about 6 hours. Then the entire reaction solution is transferred to a distillation apparatus.

At a bottom temperature beginning at 28° C. and a pressure of 30 mbar, the distillation of the raw synthesis product is started. While gradually raising the bottom temperature to 64° C. and lowering the pressure within the distillation apparatus to 2 mbar, distillate is removed until a volume of about 200 ml of liquid remains.

This remainder of the raw distillate containing the ferric chloride is returned to the synthesis apparatus of Example 1 into which 2115 g of vinylmethyldichlorosilane has already been placed. At 50° C. 584 g of hydrogen chloride was added over a period of about 6 hours. The distillation of the raw synthesis product was performed as described, and then the procedure of synthesis and raw synthesis product distillation was repeated twice again in the same manner. In the final operation the distillation is not stopped until the ferric chloride starts to separate dry at the edge of the bottom of the still.

The raw distillates from the 4 batches are combined and subjected to fractional distillation. 10,128 g of 2-chloroethylmethyldichlorosilane are obtained. This corresponds to a yield of 95.1% with respect to the input vinylmethyldichlorosilane.

EXAMPLE 14

2115 g of vinylmethyldi-chlorosilane and 42 g of tantalum chloride are placed in the apparatus of Example 1. At a reaction solution temperature of 70° C., 584 g of hydrogen chloride is introduced over a period of 6 hours. The gas chromatographic analysis of the reaction solution obtained showed the following composition (area percentages):
97% 2-chloroethylmethyldichlorosilane
0.1% vinylmethyldichlorosilane
1.5% methyltrichlorosilane
1.4% unidentified components.

This raw product was transferred to a distillation apparatus and distilled as in Example 13 until the tantalum chloride catalyst remains dry in the flask. The collected distillate was analyzed by gas chromatography and had the following composition:
97.3% 2-chloroethylmethyldichlorosilane
0.1% vinylmethyldichlorosilane
1.6% methyltrichlorosilane
1.0% unidentified components.

The fractional distillation of the distillate separated from the catalyst yielded 2592 g of 2-chloroethylmethyldichlorosilane in a purity, as determined by gas chromatography, of 99.4%. This corresponds to a yield of 96.7% with respect to the input vinylmethyldichlorosilane.

TABLE 1

|  | Example No. | | | | | | | |
| --- | --- | --- | --- | --- | --- | --- | --- | --- |
|  | 5 | 6 | 7 | 8 | 9 | 10 | 11 | 12 |
| Amount of ferric chloride put in, (weight-percent) | 1 | 2 | 2 | 5 | 5 | 10 | 10 | 15 |
| Reaction temperature (°C.) | 48 | 40 | 50 | 40 | 50 | 30 | 40 | 50 |

TABLE 1-continued

|  | Example No. | | | | | | | |
|---|---|---|---|---|---|---|---|---|
|  | 5 | 6 | 7 | 8 | 9 | 10 | 11 | 12 |
| Reaction time (hours) | 6 | 6 | 6 | 6 | 6 | 6 | 6 | 6 |
| End product analysis |  |  |  |  |  |  |  |  |
| (a) Before separation of catalyst |  |  |  |  |  |  |  |  |
| $Cl-CH_2-CH_2-(CH_3-)SiCl_2$ (GC percent) | 96.3 | 90.5 | 95.9 | 93.3 | 96.0 | 94.1 | 93.3 | 93.4 |
| $CH_3-SiCl_3$ (GC percent) | 2.0 | 1.5 | 2.1 | 1.8 | 2.3 | 1.0 | 1.8 | 3.5 |
| $CH_2=CH-(CH_3-)SiCl_2$ (GC percent) | 0.4 | 7.3 | 0.7 | 4.4 | 0.3 | 4.3 | 3.7 | 0.9 |
| Total unidentified components (GC percent) | 1.3 | 0.7 | 1.3 | 0.5 | 1.4 | 0.6 | 1.2 | 2.2 |
| (b) After separation from catalyst |  |  |  |  |  |  |  |  |
| $Cl-CH_2-CH_2-(CH_3-)SiCl_2$ (GC percent) | 96.4 | 90.7 | 96.0 | 93.5 | 96.1 | 94.0 | 93.1 | 92.9 |
| $CH_3-SiCl_3$ (GC percent) | 2.1 | 1.3 | 2.0 | 1.7 | 2.2 | 1.1 | 2.0 | 4.1 |
| $CH_2=CH-(CH_3-)SiCl_2$ (GC percent) | 0.5 | 7.1 | 0.7 | 4.3 | 0.4 | 4.2 | 3.5 | 0.9 |
| Total unidentified components (GC percent) | 1.0 | 0.9 | 1.3 | 0.5 | 1.3 | 0.7 | 1.4 | 2.1 |
| Yield of 2-chloroethylmethyldichlorosilane | 95.1 | 90.1 | 94.9 | 92.9 | 95.1 | 93.3 | 92.8 | 92.9 |

It will be understood that the specification and examples are illustrative but not limitative of the present invention and that other embodiments within the spirit and scope of the invention will suggest themselves to those skilled in the art.

We claim:

1. A method of preparing 2-chloroethyldichlorosilane comprising reacting vinyldichlorosilane with hydrogen chloride in the presence of $FeCl_3$ at a temperature between 30° and 60° C.

2. The method of claim 1, wherein the $FeCl_3$ is used in amounts between 1 and 15 wt. %, with respect to the input vinyldichlorosilane.

3. The method of claim 2, wherein the amount of $FeCl_3$ is between 1 and 10 wt. % with respect to input vinyldichlorosilane and the reaction is performed at temperatures between 40° and 50° C.

4. A method of preparing 2-chloroethyldichlorosilane comprising reacting vinyldichlorosilane with hydrogen chloride in the presence of $TaCl_5$ at a temperature between 40° and 90° C.

5. The method of claim 4, wherein the $TaCl_5$ is used in amounts between 1 and 10 wt. %, with respect to the input vinyldichlorosilane.

6. The method of claim 5, wherein the $TaCl_5$ is between 1 and 5 wt. % with respect to the input vinyldichlorosilane and the reaction is performed at temperatures between 65° and 80° C.

7. The method of claim 1, wherein immediately after the reaction, the separation of the obtained 2-chloroethyldichlorosilane is performed by distillation in the presence of the $FeCl_3$ and in the absence of deactivating compounds.

8. The method of claim 4, wherein immediately after the reaction, the separation of the obtained 2-chloroethyldichlorosilane is performed by distillation in the presence of the $TaCl_5$ and in the absence of deactivating compounds.

* * * * *